(12) United States Patent
Renauld et al.

(10) Patent No.: US 9,234,042 B2
(45) Date of Patent: Jan. 12, 2016

(54) METHOD FOR PRODUCING ANTIBODY USING "NAKED" EXPRESSION VECTOR EXPRESSING TYPE II TRANSMEMBRANE FUSION PROTEIN

(75) Inventors: Jean-Christophe Renauld, Kraainem (BE); Muriel Lemaire, Ottignies (BE); Laurie Dumoutier, Orbais (BE); Yannick Nizet, Lincent (BE); Alain Vanderplasschen, Tubize (BE); Laurent Gillet, Tenneville (BE)

(73) Assignee: DELPHI GENETICS SA, Charleroi (Gosselies) (BE)

( * ) Notice: Subject to any disclaimer, the term of this patent is extended or adjusted under 35 U.S.C. 154(b) by 378 days.

(21) Appl. No.: 13/275,845

(22) Filed: Oct. 18, 2011

(65) Prior Publication Data
US 2012/0093825 A1     Apr. 19, 2012

Related U.S. Application Data

(60) Provisional application No. 61/455,278, filed on Oct. 18, 2010, provisional application No. 61/497,107, filed on Jun. 15, 2011.

(51) Int. Cl.
| | |
|---|---|
| C12N 15/62 | (2006.01) |
| C12N 15/79 | (2006.01) |
| C07K 16/28 | (2006.01) |
| C07K 14/705 | (2006.01) |
| C07K 16/24 | (2006.01) |
| A61K 39/00 | (2006.01) |

(52) U.S. Cl.
CPC ....... *C07K 16/2875* (2013.01); *C07K 14/70575* (2013.01); *C07K 16/244* (2013.01); *C07K 16/2866* (2013.01); *A61K 2039/505* (2013.01); *C07K 2317/34* (2013.01); *C07K 2317/73* (2013.01); *C07K 2317/76* (2013.01)

(58) Field of Classification Search
None
See application file for complete search history.

(56) References Cited

FOREIGN PATENT DOCUMENTS

EP     1304375 A1 * 4/2003

OTHER PUBLICATIONS

Yang et al., DNA vesus protein immunisation for production of monoclonal antibodies against Choristoneura fumiferana ecdysone receptor (CfEcR), Vaccine, 24:3115-3126, 2006.*
Morel et al., DNA immunisation:alteringthe cellular localisation of expressed protine an immunisation route allows manipulation of the immune response, Vaccine, 22: 447-456, 2004.*
Bianchi et al., Maintenance of peripheral tolerance through controlled tissue homing of antigen-specific T cells in K14-mOVA mice, J. Immunol. 182(8):4665-4674, Apr. 15, 2009.*

(Continued)

*Primary Examiner* — Claire Kaufman
(74) *Attorney, Agent, or Firm* — Knobbe, Martens, Olson & Bear, LLP

(57) ABSTRACT

Methods are disclosed for generating antibodies and an expression vector used to express protein(s) which provoke the antibody response. The expression vector may be useful in generating an antibody directed to an antigen, comprising a gene in operable linkage with a promoter, which gene encodes upon expressing a fusion protein comprising (i) CD134L, a fragment or homologous protein thereof as N-terminal moiety of the fusion protein; and (ii) all or part of an antigenic protein as C-terminal moiety of the fusion protein. To generate the antibodies, the vector is injected into a subject animal, which produces a fusion protein, against which antibodies are generated.

12 Claims, 5 Drawing Sheets

(56) References Cited

OTHER PUBLICATIONS

Teasdale et al., The signal for golgi retention of bovine beta1,4-galactosyltransferase is in the transmembrane domain, J. Biol. Chem. 267(6): 4084-4095, Feb. 25, 1992.*

Grosenbach et al., A recombinant vector expressing transgene for four T-cell costimulatory molecules (OX40L, B7-1, ICAM-1, LFA-3) induces sustained CD4+ and CD8+ T-cell actiation, protection from apoptosis, and enhanced cytokine production, Cellular Immunol. 222:45-57, 2003.*

Boyle et al., Influence of cellular location on expressed antien on the efficacy of DNA vaccination: cytotoxic T lymphocyte and antibody responses are suboptimal when antigen id cytoplasmic after intramuscular DNA immunization, International Immunol. 9(12):1897-1906, 1997.*

Krippner-Heidenreich et al., Single-chain TNF, a TNF derivative with enhanced stbility and antitumoral activity, J. Immunol. 180:8176-8183, 2008.*

Miura et al., Molecular cloning and characterization of a novel glycoprotein, gp34, that is specifically induced by the human T-cell leukemia virus type I transactivator p40tax, Mol. Cell. Biol. 11(3):1313-1325, Mar. 1991.*

Yurai et al., Vaccines targeting tumor angiogenesis, in Cancer Reviews:New Vaccines, vol. 26, N. Elliot, Ed., (Nova Science Pub. :New York, NY),2006, p. 53.* tCompaan et al., The crystal structure of the costimulator OX40-OX40L complex, Structure, 14(8):1321-1330, Aug. 2006.*

Ishii, et al., "OX40 (CD134) and OX40 ligand interaction plays an adjuvant role during in vivo Th2 responses," Eur. J. Immunol. 2003. 33: 2372-2381.

Jenkins, et al., "Dendritic Cell Expression of OX40 Ligand Acts as a Costimulatory, Not Polarizing, Signal for Opitaml Th2 Priming and Memory Induction in Vivo," The Journal of Immunology, 2007; 179:3515-3523.

Baum, et al., "Molecular characterization of murine and human OX40/OX40 ligand systems: identification of a human OX40 ligand as the HTLV-1-regulated protein gp34," The EMBO Journal, 1994, vol. 13 No. 17 pp. 3992-4001.

* cited by examiner

A

B

SEQUENCE LISTING

```
<160> NUMBER OF SEQ ID NOS: 21

<210> SEQ ID NO 1
<211> LENGTH: 549
<212> TYPE: DNA
<213> ORGANISM: Homo sapiens

<400> SEQUENCE: 1
atggaaaggg tccaacccct ggaagagaat gtgggaaatg cagccaggcc aagattcgag      60
aggaacaagc tattgctggt ggcctctgta attcagggac tggggctgct cctgtgcttc     120
acctacatct gcctgcactt ctctgctctt caggtatcac atcggtatcc tcgaattcaa     180
agtatcaaag tacaatttac cgaatataag aaggagaaag gtttcatcct cacttcccaa     240
aaggaggatg aaatcatgaa ggtgcagaac aactcagtca tcatcaactg tgatgggttt     300
tatctcatct ccctgaaggg ctacttctcc caggaagtca acattagcct tcattaccag     360
aaggatgagg agccccctctt ccaactgaag aaggtcaggt ctgtcaactc cttgatggtg     420
gcctctctga cttacaaaga caaagtctac ttgaatgtga ccactgacaa tacctccctg     480
gatgacttcc atgtgaatgg cggagaactg attcttatcc atcaaaatcc tggtgaattc     540
tgtgtcctt                                                             549

<210> SEQ ID NO 2
<211> LENGTH: 183
<212> TYPE: PRT
<213> ORGANISM: Homo sapiens

<400> SEQUENCE: 2

Met Glu Arg Val Gln Pro Leu Glu Glu Asn Val Gly Asn Ala Ala Arg
  1               5                  10                  15

Pro Arg Phe Glu Arg Asn Lys Leu Leu Leu Val Ala Ser Val Ile Gln
                 20                  25                  30

Gly Leu Gly Leu Leu Leu Cys Phe Thr Tyr Ile Cys Leu His Phe Ser
             35                  40                  45

Ala Leu Gln Val Ser His Arg Tyr Pro Arg Ile Gln Ser Ile Lys Val
         50                  55                  60

Gln Phe Thr Glu Tyr Lys Lys Glu Lys Gly Phe Ile Leu Thr Ser Gln
```

```
                65                  70                  75                  80
Lys Glu Asp Glu Ile Met Lys Val Gln Asn Asn Ser Val Ile Ile Asn
                    85                  90                  95
Cys Asp Gly Phe Tyr Leu Ile Ser Leu Lys Gly Tyr Phe Ser Gln Glu
                100                 105                 110
Val Asn Ile Ser Leu His Tyr Gln Lys Asp Glu Glu Pro Leu Phe Gln
                115                 120                 125
Leu Lys Lys Val Arg Ser Val Asn Ser Leu Met Val Ala Ser Leu Thr
            130                 135                 140
Tyr Lys Asp Lys Val Tyr Leu Asn Val Thr Thr Asp Asn Thr Ser Leu
145                 150                 155                 160
Asp Asp Phe His Val Asn Gly Gly Glu Leu Ile Leu Ile His Gln Asn
                165                 170                 175
Pro Gly Glu Phe Cys Val Leu
            180

<210> SEQ ID NO 3
<211> LENGTH: 51
<212> TYPE: DNA
<213> ORGANISM: Artificial
<220> FEATURE:
<223> OTHER INFORMATION: synthetic DNA

<400> SEQUENCE: 3
taacattcgt cgacatttgc taactcgaga ccatggaaag ggtccaaccc c            51

<210> SEQ ID NO 4
<211> LENGTH: 101
<212> TYPE: DNA
<213> ORGANISM: Artificial
<220> FEATURE:
<223> OTHER INFORMATION: synthetic DNA

<400> SEQUENCE: 4
tattaccatg gtcatgcggc cgctaggatg tatctagaag atccgccgcc acccgaccca   60
ccaccgcccg agccaccacc accaaggaca cagaattcac c                      101

<210> SEQ ID NO 5
<211> LENGTH: 45
<212> TYPE: DNA
<213> ORGANISM: Artificial
<220> FEATURE:
<223> OTHER INFORMATION: synthetic DNA

<400> SEQUENCE: 5
atttgctaat ctagagaaca aaaattaatt tctgaagaag attta                   45

<210> SEQ ID NO 6
<211> LENGTH: 45
<212> TYPE: DNA
<213> ORGANISM: Artificial
<220> FEATURE:
<223> OTHER INFORMATION: synthetic DNA

<400> SEQUENCE: 6
atactaaatt gcggccgcta atcttcttc agaaattaat ttttg                    45

<210> SEQ ID NO 7
<211> LENGTH: 39
<212> TYPE: DNA
<213> ORGANISM: Artificial
<220> FEATURE:
```

```
<223> OTHER INFORMATION: synthetic DNA

<400> SEQUENCE: 7
atttgctaat ctagagcctt cctcatcaac aaagtgccc                                    39

<210> SEQ ID NO 8
<211> LENGTH: 41
<212> TYPE: DNA
<213> ORGANISM: Artificial
<220> FEATURE:
<223> OTHER INFORMATION: synthetic DNA

<400> SEQUENCE: 8
gttaaagatg cggccgccac caagtgtgat agcgcctcca g                                 41

<210> SEQ ID NO 9
<211> LENGTH: 33
<212> TYPE: DNA
<213> ORGANISM: Artificial
<220> FEATURE:
<223> OTHER INFORMATION: synthetic DNA

<400> SEQUENCE: 9
atactaaatt ctagaactaa actgagtatt gag                                          33

<210> SEQ ID NO 10
<211> LENGTH: 36
<212> TYPE: DNA
<213> ORGANISM: Artificial
<220> FEATURE:
<223> OTHER INFORMATION: synthetic DNA

<400> SEQUENCE: 10
atactaaatt gcggccgcaa tgagctgttg cttaca                                       36

<210> SEQ ID NO 11
<211> LENGTH: 20
<212> TYPE: DNA
<213> ORGANISM: Artificial
<220> FEATURE:
<223> OTHER INFORMATION: synthetic DNA

<400> SEQUENCE: 11
cgctggccct aggtcctcat                                                         20

<210> SEQ ID NO 12
<211> LENGTH: 28
<212> TYPE: DNA
<213> ORGANISM: Artificial
<220> FEATURE:
<223> OTHER INFORMATION: synthetic DNA

<400> SEQUENCE: 12
ccgctagcat catgcggatc gtgtgcct                                                28

<210> SEQ ID NO 13
<211> LENGTH: 30
<212> TYPE: DNA
<213> ORGANISM: Artificial
<220> FEATURE:
<223> OTHER INFORMATION: synthetic DNA

<400> SEQUENCE: 13
ggtctagatc aaagttcctc gtggtcgtgc                                              30
```

```
<210> SEQ ID NO 14
<211> LENGTH: 22
<212> TYPE: DNA
<213> ORGANISM: Artificial
<220> FEATURE:
<223> OTHER INFORMATION: synthetic DNA

<400> SEQUENCE: 14
ggcacagtct agagacccca ag                                           22

<210> SEQ ID NO 15
<211> LENGTH: 30
<212> TYPE: DNA
<213> ORGANISM: Artificial
<220> FEATURE:
<223> OTHER INFORMATION: synthetic DNA

<400> SEQUENCE: 15
gggccctgcg gccgcaagtt cctcgtggtc                                   30

<210> SEQ ID NO 16
<211> LENGTH: 33
<212> TYPE: DNA
<213> ORGANISM: Artificial
<220> FEATURE:
<223> OTHER INFORMATION: synthetic DNA

<400> SEQUENCE: 16
atactaaatt ctagatggta taaggagccc aat                               33

<210> SEQ ID NO 17
<211> LENGTH: 36
<212> TYPE: DNA
<213> ORGANISM: Artificial
<220> FEATURE:
<223> OTHER INFORMATION: synthetic DNA

<400> SEQUENCE: 17
atactaaatt gcggccgcag ttgtaactag atcatc                            36

<210> SEQ ID NO 18
<211> LENGTH: 33
<212> TYPE: DNA
<213> ORGANISM: Artificial
<220> FEATURE:
<223> OTHER INFORMATION: synthetic DNA

<400> SEQUENCE: 18
ttcagttcta gactgggcca gagatgcagc acc                               33

<210> SEQ ID NO 19
<211> LENGTH: 28
<212> TYPE: DNA
<213> ORGANISM: Artificial
<220> FEATURE:
<223> OTHER INFORMATION: synthetic DNA

<400> SEQUENCE: 19
ctcttgtcta gagcaacaga aatacaac                                     28

<210> SEQ ID NO 20
<211> LENGTH: 33
<212> TYPE: DNA
<213> ORGANISM: Artificial
<220> FEATURE:
<223> OTHER INFORMATION: synthetic DNA
```

```
<400> SEQUENCE: 20
tagcatcgcg gccgctggtc ggcttttctg cct                          33

<210> SEQ ID NO 21
<211> LENGTH: 31
<212> TYPE: DNA
<213> ORGANISM: Artificial
<220> FEATURE:
<223> OTHER INFORMATION: synthetic DNA

<400> SEQUENCE: 21
ctcagagcgg ccgctggaat gtgcacacat c                            31
```

METHOD FOR PRODUCING ANTIBODY USING "NAKED" EXPRESSION VECTOR EXPRESSING TYPE II TRANSMEMBRANE FUSION PROTEIN

CROSS-REFERENCE TO RELATED APPLICATIONS

This application claims priority of provisional application No. 61/455,278 filed Oct. 18, 2010 and of provisional application No. 61/497,107 filed Jun. 15, 2011 each incorporated by reference in its entirety.

FIELD OF THE INVENTION

The invention of the present application relates to a method for producing an antibody by gene immunization. More specifically, the invention relates to a method of enabling easy production of an antibody useful as drugs, diagnostic agents, reagents for the research, etc., and to an expression vector used in this method.

BACKGROUND AND PRIOR ART OF THE INVENTION

Since the development of recombinant DNA techniques in the late 1970s, gene fusion technology has been used for generating multifunctional proteins for a broad range of applications. Fusion proteins are utilised in protein science research for diverse applications. In order to construct such fusion proteins, two types of connection are possible. One is 'end to end' fusion in which the N-terminus of one domain is linked to the C-terminus of the other domain. The second is "insertional" fusion in which one domain is inserted in-frame into the middle of the other parent domain.

Antibodies have widely been utilized as reagents for the research for the purpose of detection, purification, elimination, inhibition of a protein or the like, because it has property of recognizing specific protein and binding thereto. Recently, it has widely been used not only as reagents for the research but also as drugs or diagnostic agents.

In producing antibodies, it has so far been general to use a method that a large amount of protein as an antigen is purified and injected to an animal or animals such as rabbits or mice to collect antibodies generated in sera. It required, however, much time and a great deal of labor to obtain a large amount of a purified antigenic protein. It is desired to provide a more convenient method for producing antibodies, accordingly.

It was reported that when a gene coding for an influenza virus nucleoprotein is integrated into an expression vector and intramuscularly injected directly as DNA to mice, then virus proteins are produced in the murine bodies and additionally the antibody against these proteins are generated in the sera (Ulmer et al., Science 259: 1745-1749, 1993). As a result, this expression vector received much attention for the use to produce antibodies. Thus, it has been designated as gene immunization that an expression vector for an antigenic protein is inoculated directly to an animal to generate and prepare antibodies. In using gene immunization, however, in some cases, the titer of the generated antibody is very low or no antibody is generated depending on the kind of the antigen used.

It was reported as an example of gene immunization that ovalbumin was fused in the downstream of transmembrane domain of transferrin receptor to form a membrane type and it was injected intramuscularly or subcutaneously to mice in order to investigate an effect of the expression site of antigenic protein on the efficacy of gene immunization. The titer of the antibodies generated, however, rather decreased since the protein was converted into a membrane type. (Boyle et al., Int. Immunol. 9: 1897-1906, 1997).

The document EP 1 304 375 refers to a method for producing an antibody against an antigenic protein, wherein the antigenic protein is fused with the C-terminal side of a transmembrane domain of which the N-terminal side is located in the cell and the C-terminal side is out of the cell and the fusion protein is inoculated in a non-human animal.

The purpose of the invention of the present application is to provide an improved method for producing antibodies directed to proteins, for which it was difficult to produce antibodies in so far known gene immunization methods.

Additionally, the purpose of the invention is to provide an expression vector useful to express an immunogen which is applied in the above-mentioned method for producing an antibody.

How these and other aspects of the invention are achieved will be seen from the disclosure which follows.

SUMMARY OF THE INVENTION

In one embodiment, an expression vector useful in generating an antibody directed to an antigen is provided. The expression vector comprises a gene in operable linkage with a promoter, which gene encodes a fusion protein upon expression. The fusion protein comprises:
  (i) CD134L, a fragment or homologous protein thereof as N-terminal moiety of the fusion protein; and
  (ii) all or part of an antigenic protein as C-terminal moiety of the fusion protein.

CD134L is a type II transmembrane belonging to the TNF receptor family. The protein consists of a short N terminal cytosolic tail and a large C terminal extracellular domain. It is expressed on the cell surface as a trimer, preferentially on activated B cells (Miura et al., Mol Cell Biol 11, 1313-1325 (1991); Croft, M., Annu Rev Immunol 28, 57-78 (2010)). According to the present invention this type II transmembrane protein is suitable as carrier for cell surface expression of antigens fused to its carboxyterminal end (FIG. 1). The fusion protein is expressed and the antigenic protein which is fused to the carboxyterminal end of CD134L is expressed on the cell surface. Therefore, the construct is suitable for the production of antibodies. Any CD134L, a fragment or homologous protein thereof is suitable as N-terminal carrier moiety as long as the function is as for example that of human CD134L. CD134L proteins and their homologues are found in diverse animal species such as vertebrate, fish (including agnatha, chondrichthyes, osteichthyes), amphibian, reptile, avian or mammalian animal species. In a preferred embodiment of the expression vector said CD134L is mammalian CD134L. In a further preferred embodiment said CD134L is human CD134L. In yet another preferred embodiment said CD134L is rodent CD134L.

In a further preferred embodiment, the CD134L comprises or consists of a amino acid sequence shown in SEQ ID NO: 2.

In an embodiment, the fragment of CD134L is a biologically active fragment of CD134L and comprises the cytosolic and transmembrane domain, preferably the fragment of CD134L—used in the above described fusion protein as "CD134L moiety"—is a polypeptide having at least the amino acid sequence from amino acid position 1 to 50 of SEQ ID NO: 2, preferably at least from amino acid position 1 to 60 of SEQ ID NO: 2, further preferred at least from amino acid position 1 to 80, even further preferred at least from amino acid position 1 to 100, more preferred at least from amino acid position 1 to 120, still further preferred at least from amino acid position 1 to 140 and most preferred at least from amino acid position 1 to 160 of the amino acid sequence shown in SEQ ID NO: 2.

In one embodiment, the nucleic acid sequence coding for the CD134L-moiety is selected from:
(a) a polynucleotide encoding a protein having the amino acid sequence shown in SEQ ID NO: 2;
(b) a polynucleotide encoding a protein which protein has at least 60% identity to the amino acid sequence of the protein of (a);
(c) a polynucleotide encoding a protein having an amino acid sequence comprising a deletion, substitution, insertion and/or addition of one to 75 amino acid residues with respect to the amino acid sequence shown in SEQ ID NO: 2;
(d) a polynucleotide having a nucleotide sequence shown in SEQ ID NO: 1;
(e) a polynucleotide hybridizing under the stringent conditions comprising a wash in a solution of 1× sodium chloride/sodium citrate (SSC) and 0.1% sodium dodecyl sulfate (SDS) at 65° C. to the full complement of the polynucleotide having a nucleotide sequence shown in SEQ ID NO: 1.

In a further embodiment, the antigenic protein as C-terminal moiety of the fusion protein, which fused to the CD134L moiety, is 10 to 1000, 10 to 500, 10 to 400, 10 to 300, 10 to 200, 10 to 150, 10 to 100, 10 to 80, 10 to 60, 10 to 50, 10 to 40, 10 to 30, 10 to 20, 5 to 15 and 5 to 10 amino acid residues in length. In another embodiment, the antigenic protein is having a length of at least 20, 30, 50, 80, 100, 150, 200, 300, 400, 500, 600, 700, 800 amino acid residues in length, or preferably 20 to 1000, 20 to 500, 30 to 500, 50 to 500, 80 to 500, 100 to 500, 150 to 500, 200 to 500, 300 to 500, 400 to 500, 500 to 1000, 600 to 1000, 800 to 1000 and 900 to 1000 amino acid residues in length.

In another embodiment of the expression vector, the promoter may be any one of SV40 early and late promoters, CMV promoter (immediate-early promoter-regulatory region of human cytomegalovirus) and promoters of retroviral LTRs, such as those of the Rous sarcoma virus ("RSV"), metallothionein promoters, such as the mouse metallothionein-I promoter.

Further, the expression vector may comprise a sequence coding for a linker peptide interposed between (i) and (ii). This means that the fusion protein comprises an amino acid sequence wherein CD134L, a fragment or homologous protein thereof as N-terminal moiety is connected to the antigenic protein (C-terminal moiety) by a linker peptide. Such linker peptide preferably is $(G_4S)_3$.

In one embodiment, a recombinant cell, transformed or transfected with the expression vector as described above is provided. Preferably, the recombinant cell is a eukaryotic cell.

Also provided is a method for producing an antibody specific for an antigen comprising administering the expression vector of claim 1 to a subject animal, wherein said expression vector comprises a gene in operable linkage with a promoter, which gene encodes upon expressing a fusion protein comprising (i) CD134L, a fragment or homologous protein thereof as N-terminal moiety of the fusion protein, and (ii) all or part of an antigenic protein as C-terminal moiety of the fusion protein, and said antibody is generated in the subject animal.

In one embodiment, the method comprises a step of administering the expression vector via electroporation. In this preferred embodiment the expression vector is administered "as is" to a subject animal, also referred to as "naked" DNA or expression vector. According to this method of administering said expression vector via electroporation said expression vector is administered into the subject animal by DNA electrotransfer, which method comprises the steps of intramuscular injection of the DNA and applying electric pulses to the skin of the subject animal close to the injection site.

In an alternative embodiment, the expression vector is administered to a subject animal after transformation or transfection into a cell capable of a expressing the fusion protein on its surface.

Accordingly, the method may comprise a step of administering the recombinant cell transformed or transfected with the expression vector of the present invention as described above to a subject animal, wherein said expression vector produces a fusion protein of (i) and (ii) on the surface of said recombinant cell, under conditions favoring the generation of antibodies specific to (ii) by said subject animals.

In one embodiment, the antigenic protein is autologous to the subject animal. In particular, the antigenic protein is autologous to the subject animal and the CD134L protein is foreign to the subject animal. The antigenic protein can be any protein including proteins for the subject animal because it may be possible to induce an antibody response against self-antigens, and therefore breaking natural tolerance.

In a further embodiment, the method may comprise recovering the generated antibody from the serum of the subject animal.

In yet another embodiment, the method may comprise the following steps:
(i) recovering cells from the spleen of the subject-animal which produce the antibody;
(ii) immortalizing the cells to generate hybridoma cell producing the antibody;
(iii) culturing the hybridoma cell in a medium wherein the antibody accumulates in the medium; and
(iv) recovering monoclonal antibodies from the culture medium.

DETAILED DESCRIPTION OF THE INVENTION

This invention relates to a method of generating antibodies. More particularly, the method involves administering an expression vector wherein a nucleic acid molecule encoding a cell surface type 2 transmembrane protein is concatenated to a nucleic acid molecule encoding an antigen of interest, where the nucleic acid molecule encoding the antigen of interest is fused to the type 2 transmembrane proteins in the form of an expression vector in operable linkage with a promoter, can be administered as "naked DNA," or following transformation or transfection of a recipient cell, where the cell is administered.

Figure 1:
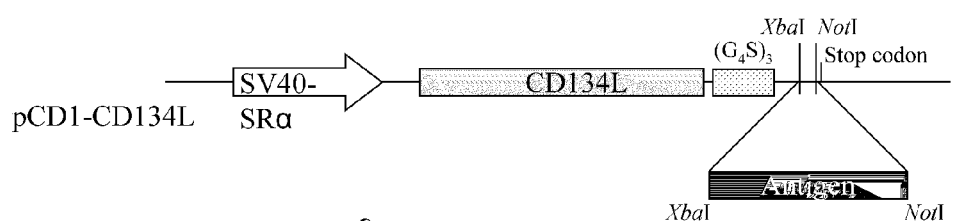
FIG. 1 shows the expression of antigens as cell surface type II membrane fusion proteins. Panel A is a schematic representation of the pCD1-CD134L vector constructed in order to express antigens fused to the carboxyterminal end of human CD134L. Panel B is a schematic representation of transgene expression as a trimeric cell surface protein.
Figure 1:
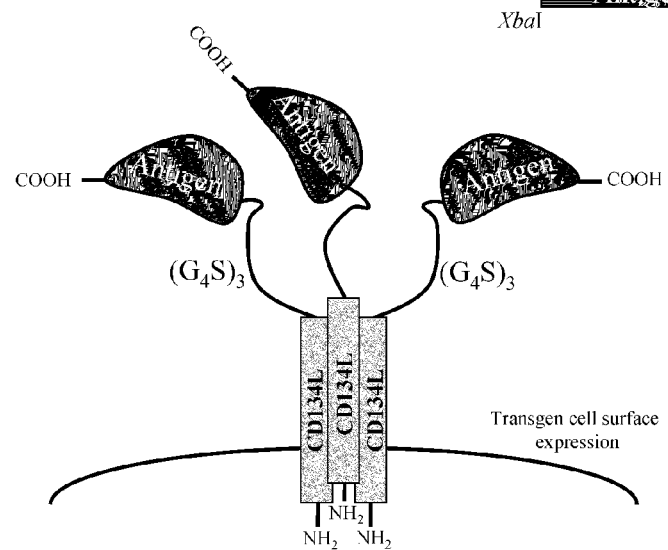
Figure 2:
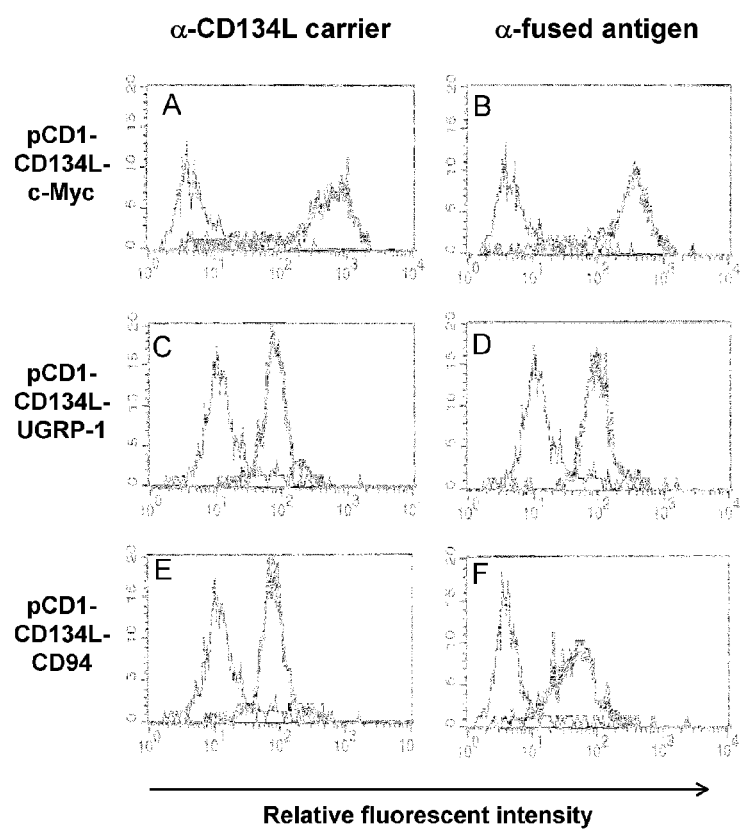
FIG. 2 shows the cell surface expression of antigens fused to the carboxyterminal end of CD134L. pCD1-CD134L derived vectors were constructed to express portion of c-Myc, UGRP-1 and CD94 antigens fused to CD134L (Table 1, AA cloned). IR983F cell lines stably expressing the fusion protein were produced. Untransfected cells (U) or transfected cells (T) were treated for cell surface indirect immunofluorescent staining of the CD134L carrier (Panels A, C, and E) or the staining of c-Myc, (Panel B), UGRP-1 (Panel D) or CD94 (Panel F) and then analysed by flow cytometry.

CD134L is a type II transmembrane belonging to the TNF receptor family. The protein consists of a short N terminal cytosolic tail and a large C terminal extracellular domain. It is expressed on cell surface as a trimer, preferentially on activated B cells (Miura et al., *Mol Cell Biol* 11, 1313-1325 (1991); Croft, M., *Annu Rev Immunol* 28, 57-78 (2010)). In some studies, the inventors tested whether this type II transmembrane protein could be used as carrier for cell surface expression of antigens fused to its carboxyterminal end. To test this hypothesis, a vector nicknamed pCD1-CD134L was constructed as described in detail in the examples (see FIG. 1). Next, epitopes derived from human c-Myc (here a peptide of 10 amino acid residues), UGRP-1 (here a polypeptide of 73 amino acid residues) and CD94 (here a polypeptide of 144 amino acid residues) were cloned in the pCD1-134L vector. IR983F cells were then stably transfected with the resulting vectors. Derived cell lines resistant to hygromycin were then stained for indirect immunofluorescent detection of cell surface expression of the CD134L and the fused antigens (FIG. 2). The results presented in FIG. 2 demonstrate that the fusion of antigens varying in length between 10 and 144 amino acid residues, and derived from different protein types, to the carboxyterminal end of the CD134L did not prevent its cell surface expression (FIG. 2, panels A, C and E). Immunofluorescent staining raised against the fused antigens confirmed their cell surface expression (FIG. 2, panels B, D and F).

The data presented demonstrate that fusion of antigens at the carboxyterminal end of the CD134L type II protein is an efficient method to induce their cell surface expression. In comparison to type I protein carriers, the type II CD134L carrier has the major advantage to allow the cloning of the antigen in frame of the carboxyterminal end; thereby avoiding any interference with the anchor signal located at the N terminal end. Next, the potential was tested of the pCD1-CD134L vector in an immunization scheme relying on the injection of histocompatible living cells stably expressing the antigen fused to the CD134L. The data presented below demonstrate that this method was used successfully to produce mouse antibodies raised against IRCAL (*Ixodes ricinus* calreticulin: Tick secreted protein) and rat monoclonal antibodies (Mabs) raised against a domain (40 amino acid residues in length) of Vaccinia Virus A56 (type I transmembrane protein).

Figure 3:
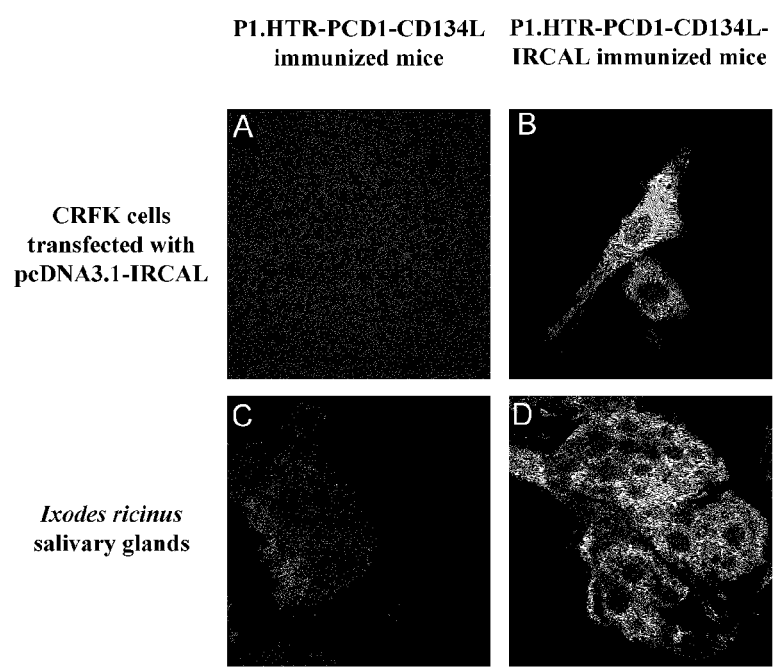
FIG. 3 shows the production of anti-IRCAL antibodies. Mice were immunized with live P1.HTR cell lines stably transfected with pCD1-CD134L or pCD1-CD134L-IRCAL. Sera were collected from the animals and used for indirect immunofluorescent staining of CRFK cells transfected with pcDNA3.1-IRCAL vector and *Ixodes ricinus* salivary glands. Cells were mounted and analysed by confocol microscopy. The side of panels A-B and C-D corresponds to 75 and 200 µm of the specimen, respectively.

For production of mouse antibodies raised against IRCAL, most of IRCAL ORF (amino acid residues 17-413) was cloned in the pCD1-CD134L vector. The resulting pCD1-CD134L-IRCAL plasmid was stably transfected in P1.HTR cells. Cell surface expression of the transgene was controlled by indirect immunofluorescent staining using the rat Mab LO-CD134L (data not shown). Mice were immunized by injection of stably transfected living cells as described in the examples. At the end of the immunization protocol, sera were collected and analysed for the presence of anti-IRCAL antibodies by indirect immunofluorescent staining of cells transiently expressing IRCAL (FIG. 3, panel B). All immunized mice (n=10) had detectable antibodies raised against IRAC with titre ranging from 1/512 up to 1/4096 (highest dilution leading to a positive signal). Finally, the ability of the antibodies produced was controlled to react against the native protein expressed in *Ixodes ricinus*. Tick salivary glands were treated for indirect immunofluorescent staining and analysed by confocal microscopy (FIG. 3, panel D). Confocal examination of the samples demonstrated that the antibodies produced recognised a protein abundantly expressed in the endoplamsic reticulum and secretary vesicles.

The immunisation method developed in the present study was also used to produce rat Mabs raised against a domain of Vaccinia virus A56 (AA 48-88). This domain is conserved amongst orthopoxviruses such as Variola virus (smallpox), monkeypox, cowpox and ectromelia. A IR983F cell line stably transfected with the pCD1-CD134L-A56 vector was produced and cell surface expression of the transgene was controlled by flow cytometry. Next, an histocompatible LOU-C rat was immunised with irradiated living cells. The serum collected from the rat at the end of the immunization protocol contained high titre (1/8192; highest dilution leading to a positive signal) of anti-Vaccinia virus antibodies as revealed by indirect immuofluorescent staining of viral plaques (data not shown). Rat spleen was used to produce Mabs. From a single fusion, the three step screening described in the methods led to the selection of 7 stable hybridomas secreting Mabs inducing a strong staining of VV infected cells. Among these Mabs, four were IgG2b, two were IgG1 and one was an IgG2a, demonstrating that the immunization procedure used induced isotype switching and probably antibody affinity maturation. The results obtained with one of them (Mab A56VV1) are presented in FIG. 4.

The property of the type II transmembrane CD134L to act as a carrier for cell surface expression of antigens fused to its carboxyterminal end has been demonstrated. This property was established for antigens between 10 up to 396 AA and derived from different protein types. The cell surface expression of CD134L as a trimer could consequently contribute to the immunogenicity of the CD134L-antigen fusion proteins observed in the present study.

In addition, variants of the CD134L moiety may also be used, which variants preferably have at least 60% identity, further preferred at least 70% identity, still further preferred at least 80% identity, particularly preferred at least 90% identity, more preferred at least 95% identity, even more preferred at least 98% and most preferred at least 99% identity to SEQ ID NO: 2.

Further, variants of the CD134L moiety may also be used, said variants being represented by a protein having an amino acid sequence comprising a deletion, substitution, insertion and/or addition of one to 75 more amino acids with respect to the amino acid sequence shown in in SEQ ID NO: 2. In a preferred embodiment 1 to 60, preferred 1 to 50, more preferred 1 to 40, further preferred 1 to 30, still further preferred 1 to 20, even further preferred 1 to 15, more preferred 1 to 10, further preferred 1 to 5, and most preferred 1, 2, 3 or 4 amino acids are deleted, substituted, inserted and/or added in respect to the sequence shown in SEQ ID NO: 2. The term "addition" means N-terminal or C-terminal addition of amino acid residues in respect to above mentioned sequences.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2:482 (1981), by the homology alignment algorithm of Needleman and Wunsch J. Mol. Biol. 48:443 (1970), by the search for similarity method of Pearson and Lipman Proc. Natl. Acad. Sci. U.S.A. 85:2444 (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms "substantial identity" or "substantial sequence identity" mean that two polypeptide sequences, when optimally aligned, such as by the programs GAP or BESTFIT using default gap weights, share at least 80 percent sequence identity, preferably at least 90 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

Functional Equivalents

The terms "functional equivalents" and "functional variants" are used interchangeably herein. Functional equivalents of CD134L encoding DNA are isolated DNA fragments that encode a polypeptide that exhibits a particular function of the CD134L, which may also be maintained in a fusion construct. A functional equivalent of a CD134L polypeptide is a polypeptide that is anchored in the cell membrane. Functional equivalents therefore also encompass biologically active fragments.

Functional protein or polypeptide equivalents may contain only conservative or homologous substitutions of one or more amino acids in the amino acid sequences shown in SEQ ID NO: 2 or substitutions, insertions or deletions of non-essential amino acids. Accordingly, a non-essential amino acid is a residue that can be altered in an amino acid sequence shown in SEQ ID NO: 2 without substantially altering the biological function. For example, amino acid residues that are conserved among the CD134L proteins are predicted to be particularly unamenable to alteration. Furthermore, amino acids conserved among the CD134L proteins and other CD134L are not likely to be amenable to alteration.

The term "conservative substitution" or substitution by "homologous" amino acid residues is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Conservative amino acid substitutions usually have minimal impact on the activity of the resultant protein. Such substitutions are described below. Conservative substitutions replace one amino acid with another amino acid that is similar in size, hydrophobicity, charge, polarity, steric features, aromaticity etc. Such substitutions generally are conservative when it is desired to finely modulate the characteristics of the protein.

"Homologous" amino acid residues as used herein refer to amino acid residues which have similar chemical properties concerning hydrophobicity, charge, polarity, steric features, aromatic feature etc. Examples for amino acids which are homologous to each other include in terms of positive charge lysine, arginine, histidine; in terms of negative charge: glutamic acid, aspartic acid; in terms of hydrophobicity: glycine, alanine, valine, leucine, isoleucine, proline, phenylalanine; in terms of polarity serine, threonine, cysteine, methionine, tryptophan, tyrosine, asparagine, glutamine; in terms of aromaticity: phenylalanine, tyrosine, tryptophan; in terms of chemically similar side groups: serine and threonine; or glutamine and asparagines; or leucine and isoleucine.

Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Functional nucleic acid equivalents may typically contain silent mutations or mutations that do not alter the biological function of encoded polypeptide. Accordingly, the invention provides nucleic acid molecules encoding a fusion protein comprising a CD134L moiety that contain changes in amino acid residues that are not essential for a particular biological activity. Such proteins differ in the amino acid sequence shown in SEQ ID NO: 2 yet they retain the biological activity as defined herein. In one embodiment the isolated nucleic acid molecule comprises a nucleotide sequence encoding a protein, wherein the protein has a percent identity of at least about 60%, 65%, 70%, 75%, 80%, 85%, 90%, 95%, 96%, 97%, 98%, 99% or more to the amino acid sequence shown in of SEQ ID NO: 2.

For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, supra, and the references cited therein.

An isolated nucleic acid molecule encoding a protein homologous to the protein shown in SEQ ID NO: 2 can be created by introducing one or more nucleotide substitutions, additions or deletions into the coding nucleotide sequences such that one or more amino acid substitutions, deletions or insertions are introduced into the encoded protein. Such mutations may be introduced by standard techniques, such as site-directed mutagenesis and PCR-mediated mutagenesis.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

Also, nucleic acids encoding other CD134L family members, which thus have a nucleotide sequence that differs from one or more nucleotide sequence disclosed herein can be used for constructing a fusion construct. Such nucleic acid molecules corresponding to variants (e.g. natural allelic variants) and homologues of the DNA can be isolated based on their homology to the nucleic acids disclosed herein using the cDNAs disclosed herein or a suitable fragment thereof, as a hybridisation probe according to standard hybridisation techniques preferably under highly stringent hybridisation conditions.

The term "functional equivalents" also encompasses orthologues of the CD134L protein used herein. Orthologues of the CD134L protein are proteins that can be isolated from other species and possess a similar or identical biological activity. Such orthologues can readily be identified as comprising an amino acid sequence that is substantially homologous to the amino acid sequences shown in SEQ ID NO: 2.

In addition to naturally occurring allelic variants of the sequences provided herein, the skilled person will recognise that further changes can be introduced by mutation into the nucleotide sequences encoding the CD134 moiety thereby leading to changes in the amino acid sequence of the CD134L protein without substantially altering the function of the protein.

In a further embodiment, the CD134L has an amino acid sequence encoded by an isolated nucleic acid fragment capable of hybridising to a nucleic acid, preferably under highly stringent hybridisation conditions. Accordingly, the CD134L is a protein which comprises an amino acid sequence having at least about 90%, 95%, 96%, 97%, 98%, 99% or more identity to the amino acid sequence shown in SEQ ID NO: 2.

Protein Fragments

The invention makes use of CD134L fusion protein for generating antibodies. The CD134L moiety include biologically active fragments thereof.

Biologically active fragments of a polypeptide of the invention include polypeptides comprising amino acid sequences sufficiently identical to or derived from the amino acid sequence of the CD134L (e.g., the amino acid sequence shown in SEQ ID NO: 2), which include fewer amino acids than the full length protein, and exhibit at least one biological activity of the corresponding full-length protein, namely that the protein is properly anchored in the cell membrane. In a preferred embodiment, a fusion protein comprises at least one biologically active fragment of a CD134L according to the invention. A biologically active fragment of CD134L may comprise the cytosolic and transmembrane domain, preferably a polypeptide having at least the amino acid sequence from amino acid position 1 to 50 of SEQ ID NO: 2, or preferably at least from amino acid position 1 to 60 of SEQ ID NO: 2. Within the fusion protein, the term "operatively linked" is intended to indicate that the CD134L and the non-CD134L polypeptide are fused in-frame to each other to the C-terminus of the CD134L. The non-CD134L polypeptide serves as antigenic protein, for raising antibodies directed to said antigenic protein.

The invention also makes use of nucleic acid fragments that encode the above biologically active fragments of the CD134L.

Fusion Proteins

CD134L, or a biologically active portion thereof, can be operatively linked to a non-CD134L polypeptide (e.g., heterologous amino acid sequences) to form fusion proteins. As used herein, a CD134L "chimeric protein" or "fusion protein" comprises a CD134L polypeptide operatively linked to a non-CD134L polypeptide.

A chimeric or fusion protein may be produced by standard recombinant DNA techniques. For example, DNA fragments coding for the different polypeptide sequences are ligated together in-frame in accordance with conventional techniques, for example by employing blunt-ended or staggered-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992).

Polynucleotides

In one embodiment, an expression vector comprising a gene encoding a fusion protein is contemplated. The polynucleotide encoding the CD134L moiety of the fusion protein may be human CD134L, a fragment or homologous protein thereof (i.e. functional equivalent). In particular, the polynucleotide encoding the CD134L moiety of the fusion protein may be any polynucleotide hybridisable under stringent conditions, preferably under highly stringent conditions, to a polynucleotide comprising the nucleotide sequence shown in SEQ ID NO: 1.

As used herein, the terms "gene" and "recombinant gene" refer to nucleic acid molecules which may be isolated from chromosomal DNA, which include an open reading frame encoding a protein, e.g. human CD134L. A gene may include coding sequences, non-coding sequences, introns and regulatory sequences. Moreover, a gene refers to an isolated nucleic acid molecule as defined herein.

A nucleic acid molecule, such as a nucleic acid molecule having the nucleotide sequence shown in SEQ ID NO: 1 or a functional equivalent thereof may be isolated using standard molecular biology techniques and the sequence information provided herein. For example, a nucleic acid sequence having the sequence shown in SEQ ID NO: 1 can be isolated using standard hybridization and cloning techniques (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989).

Moreover, a nucleic acid molecule encompassing all or a portion of the nucleic acid sequence shown in SEQ ID NO: 1 can be isolated by the polymerase chain reaction (PCR) using synthetic oligonucleotide primers designed based upon the sequence information contained in SEQ ID NO: 1.

In another embodiment, an isolated nucleic acid molecule may comprise a nucleic acid molecule which is a complement of the nucleotide sequence shown in SEQ ID NO: 1 or a functional equivalent of these nucleotide sequences. A nucleic acid molecule that is complementary to another nucleotide sequence is one that is sufficiently complementary to the other nucleotide sequence such that it can hybridize to the other nucleotide sequence thereby forming a stable duplex.

In one aspect, isolated nucleic acid molecules may be provided that encode a polypeptide as described herein or a functional equivalent thereof such as a biologically active fragment or domain, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules.

Also referred herein are isolated nucleic acids that comprise DNA or RNA sequences (polynucleotides) encoding the CD134L moiety of the fusion protein. The nucleic acids may further comprise vectors for expression of the fusion protein of the invention. It is understood by one of ordinary skill in the art that because of the degeneracy in the genetic code, substitutions in the nucleotide sequence may be made which do not result in changes in the encoded amino acid sequence. It is further understood by one of ordinary skill in the art that both complementary strands of any DNA molecule described herein are included within the scope.

As used herein, the term "vector" refers to a vehicle made of a polynucleotide or which contains a polynucleotide which can transfer a polynucleotide sequence or gene of interest to a target cell. The vector may be a "viral vector" or a "plasmid vector" or may combine both properties in one construct. Examples of a vector include vectors which are capable of self replication or capable of being incorporated into a chromosome within host cells (e.g., prokaryotic cells, yeast, animal cells, plant cells, insect cells, whole animals, and whole plants), and contain a promoter at a site suitable for transcription of a polynucleotide or gene.

As used herein, the term "expression vector" refers to a nucleic acid sequence comprising a structural gene and a promoter for regulating expression thereof, and in addition, various regulatory elements in a state that allows them to operate within host cells. The regulatory element may include, preferably, terminators, selectable markers such as drug-resistance genes (e.g., a kanamycin resistance gene, a hygromycin resistance gene, etc.), and enhancers. It is well known to those skilled in the art that the type of an organism, expression vector and the type of a regulatory element may vary depending on the host cell.

As used herein, the term "promoter" refers to a base sequence which determines the initiation site of transcription of a gene and is a DNA region which directly regulates the frequency of transcription. Transcription is started by RNA polymerase binding to a promoter. The DNA insert should be operatively linked to an appropriate promoter, such as the SV40 early and late promoters, CMV promoter (immediate-early promoter-regulatory region of human cytomegalovirus) and promoters of retroviral LTRs, such as those of the Rous sarcoma virus ("RSV"), metallothionein promoters, such as the mouse metallothionein-I promoter, to name a few. The skilled person will know other suitable promoters. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

As used herein, the terms "transformation", "transduction" and "transfection" are used interchangeably unless otherwise mentioned, and refers to introduction of a nucleic acid into host cells. As a transformation method, any technique for introducing DNA into host cells can be used, including various well-known techniques, such as, for example, the electroporation method, the particle gun method (gene gun), the calcium phosphate method, and the like.

As used herein, the term "transformant" refers to the whole or a part of an organism, such as a cell, which is produced by transformation. Examples of a transformant include prokaryotic cells, such as bacteria (e.g. *Escherichia coli*), and eukaryotic cells such as yeast, animal cells, plant cells, insect cells and the like. Transformants may be referred to as transformed cells, transformed tissue, transformed hosts, or the like, depending on the subject. As used herein, all of the forms are encompassed, however, a particular form may be specified in a particular context.

Hybridisation

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, more preferably at least 95% homologous to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide used to specifically hybridize to a portion of a nucleic acid, since such a polynucleotide would hybridize to any nucleic acid molecule containing a poly (A) stretch or the complement thereof (e.g., practically any double-stranded cDNA clone).

Antibodies

Production of antibodies are provided, such as monoclonal or polyclonal antibodies that specifically bind to the antigenic protein moiety of the fusion protein encoded by one or more expression vectors disclosed herein.

As used herein, the term "antibody" (Ab) or "monoclonal antibody" (Mab) is meant to include intact molecules as well as antibody fragments (such as, for example, Fab and F(ab')2 fragments) which are capable of specifically binding to an antigenic protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies may be prepared by any of a variety of methods. For example, cells expressing a fusion protein having an antigenic protein or an antigenic fragment thereof fused C-terminally to CD134L can be administered to an animal in order to induce the production of sera containing polyclonal antibodies. In one method, the antibodies are monoclonal antibodies (or specific binding fragments thereof). Such monoclonal antibodies can be prepared using hybridoma technology (Kohler et al., *Nature* 256:495 (1975); Kohler et al., *Eur. J. Immunol.* 6:511 (1976); Hammerling et al., In: *Monoclonal Antibodies and T-Cell Hybridomas*, Elsevier, N.Y., pp. 563-681 (1981)). In general, such procedures involve immunizing an animal (preferably a mouse) with a protein or with a cell expressing a protein. The splenocytes of such mice are extracted and fused with a suitable myeloma cell line. Any suitable myeloma cell line may be employed; however, it is preferably to employ the parent myeloma cell line (SP2O), available from the American Type Culture Collection, Rockville, Md. After fusion, the resulting hybridoma cells are selectively maintained in HAT medium, and then cloned by limiting dilution as described by Wands et al. (*Gastro-enterology* 80:225-232 (1981)). The hybridoma cells obtained through such a selection are then assayed to identify clones, which secrete antibodies capable of binding the respective protein antigen.

In particular, various host animals can be immunized by administering the expression vector encoding the fusion protein carrying the a polypeptide of interest. Examples of suitable host animals include rabbits, mice, guinea pigs, and rats. Such antibodies can be of any immunoglobulin class including IgG, IgM, IgE, IgA, IgD, and any subclass thereof. The hybridomas producing the mAbs can be cultivated in vitro or in vivo.

Once produced, polyclonal or monoclonal antibodies are tested for specific recognition of a protein disclosed herein or a functional equivalent thereof in an immunoassay, such as a Western blot or immunoprecipitation analysis using standard techniques, e.g., as described in Ausubel et al., supra. Antibodies that specifically bind to a protein disclosed herein or functional equivalents thereof may also be useful.

Preferably, antibodies are produced using fragments of the protein(s) disclosed herein, wherein the fragments may be likely to be antigenic, by criteria such as high frequency of charged residues. For example, such fragments may be generated by standard techniques of PCR, and then cloned into the expression vector encoding the fusion protein.

Alternatively, techniques described for the production of single chain antibodies (U.S. Pat. Nos. 4,946,778 and 4,704,692) can be adapted to produce single chain antibodies against a protein disclosed herein or functional equivalents thereof. Kits for generating and screening phage display libraries are commercially available e.g. from Pharmacia.

Polyclonal and monoclonal antibodies that specifically bind a protein or functional equivalents thereof can be used, for example, to detect expression of a gene encoding a protein according or a functional equivalent thereof. Examples of suitable assays include, without limitation, Western blotting, ELISA's, radio immune assays (RIA's), and the like.

By "specifically binds" is meant that an antibody recognizes and binds a particular antigen but does not substantially recognize and bind other unrelated molecules in a sample.

Antibodies can be purified, for example, by affinity chromatography methods in which the polypeptide antigen is immobilized on a resin.

An antibody (e.g. a monoclonal antibody) directed against a protein disclosed herein can be used to isolate the protein by standard techniques, such as affinity chromatography or immunoprecipitation. Moreover, such an antibody can be used to detect the protein (e.g., in a cellular lysate or cell supernatant) in order to evaluate the abundance and pattern of expression of the protein.

Coupling the antibody to a detectable substance can facilitate detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, [beta]-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin.

EXAMPLES

Example 1

Preparation of an Expression Vector

An expression vector, referred to as "pCD1-CD134L" was constructed in order to determine if CD134L could be used as a carrier for the cell surface expression of antigens which have been bound to its carboxy terminus.

To construct this vector, pCD1 was used. pCD1 is a derivative of pEBS-PL, taught by Bontron, et al., *Mol. Cell. Biol.*, 17:4249-4258 (1997), incorporated by reference, which encodes a β-lactamase gene to permit bacterial selection, and "hph76," which is a gene which provides hygromycin resistance, driven by the SV40 early promoter.

To prepare the expression vector, cDNA for human type II transmembrane protein CD134L cDNA, as taught by Miura, et al., *Mol. Cell. Biol.*, 11:1313-1325 (1991), incorporated by reference in its entirety, followed by a $(G_4S)_3$ coding linker, an XbaI/NotI cloning site, and a stop codon, were inserted downstream of the SR alpha promoter (Takebe, et al., *Mol. Cell. Biol.*, 8:466-472 (1988)), using SalI and KpnI restriction sites.

To elaborate on this insert, it was obtained via RT-PCR, using well known methods, on mRNA that had been extracted from EBV immortalized human B lymphocytes that expressed CD134L. The oligonucleotide primers of SEQ ID NO: 3 and 4 were used in the RT-PCR in order to amplify the polynucleotide having the sequence shown in SEQ ID NO: 1 encoding human CD134L protein. SEQ ID NO: 2 shows the amino acid sequence of human CD134L.

Following this, antigenic domains from human proteins c-Myc, VGRP-1, and CD94 as well as either a portion of tick calreticulin, or a protein of Vaccinia virus were cloned into this vector, with the ORF encoding the antigen being cloned in fusion, downstream of the linker, using the XbaI and NotI restriction sites referred to, supra.

Example 2

Preparation of Nucleic Sequences Encoding the Antigenic Moiety

This example elaborates on the antigens referred to supra. Portions of 5 different antigens were cloned using PCR into the pCD1-CD134L vector. Specifically, cDNA encoding amino acids 410-419 of c-Myc; 21-93 of UGRP-1, 36-179 of CD94, 17-413 of tick calreticulin ("IRCAL"), and 48-87 of Vaccinia virus A56 were cloned into the vector described supra, using the primers of SEQ ID NOs: 5-17. These primers were designed to create XbaI and NotI restriction sites at the 5' and 3' ends, in order to clone them in frame with the $(G_4S)_3$ linker.

In detail, a cDNA encoding *Ixodes ricinus* calreticulin (IRCAL) (Xu et al., *J Parasitol* 91, 1326-31 (2005)) was produced by RT-PCR reactions on mRNA purified from tick salivary glands as described elsewhere (Daix et al., *Insect Mol Biol* 16, 155-66 (2007)). RT reactions were performed on 150 ng of *I. ricinus* salivary gland mRNA using SuperScript III First-Strand Synthesis System for RT-PCR Kit (Invitrogen). The Oligo(dT)$_{20}$ provided in the kit was used for this reaction. Finally, cDNA product was amplified by PCR using the IRCALfw1 primer (SEQ ID NO: 11) and the reverse primer Oligo(dT)$_{20}$. RT-PCR products were TA-cloned into the pGEM-T easy vector (Promega) and sequenced. Next, IRCAL ORF was cloned by PCR in the pcDNA3.1(+) eucaryotic expression vector (Invitrogen) resulting in pcDNA3.1-IRCAL. The PCR reaction was performed using the forward IRCALfw2 primer (SEQ ID NO: 12) containing a 5' NheI site and nucleotides 1-17 (nucleotides 1-3 encode the initiation methionine) and the reverse IRCALrev2 primer (SEQ ID NO: 13) corresponding to the ORF 3' end (nucleotides 1221-1239), the stop codon, and a XbaI site.

The Human c-Myc epitope corresponding to AA 410-419 was created by PCR using the cMycfw and cMycrev primers (SEQ ID NO: 5 and SEQ ID NO: 6). Human Uterogloblin-related protein 1 (UGRP-1) (A21 to V93) coding sequence without signal peptide was recovered from a subcloned cDNA kindly provided by Dr A. Bernard (Unit of Industrial Toxicology and Occupational Medicine, Université Catholique de Louvain) (Niimi et al., Mol. *Endocrinol.* 15, 2021-2036 (2001)). Human CD94 coding sequence corresponding to the extracellular domain (T36 to I179) of the protein was amplified by PCR using a human CD94 subclone as template (ATCC 99596). IRCAL ORF without its signal peptide was amplified by PCR using pcDNA3.1-IRCAL as template, the forward primer IRCALfw3 (SEQ ID NO: 14) containing a 5' XbaI site and nucleotides 49-57 and the reverse primer IRACLrev3 (SEQ ID NO: 15) corresponding to the 3' end of the ORF (nucleotides 1225-1239) and a 5' NotI site. The amplicon was then cloned by XbaI/NotI digestion into the pCD1-CD134L vector, resulting in pCD1-CD134L-IRCAL. A region of the A56 protein (W48 to I87) encoded by VV Lister strain was amplified by PCR using the primers shown in SEQ ID NO: 16 and SEQ ID NO: 17 and viral NA as template. The amplified region is conserved amongst various orthopoxviruses including Variola virus and is part of the extracellular domain of the protein.

Once these antigenic regions were cloned into the vector, P1.HTR cells (Van Pel, et al., *Somat. Cell Mol. Genet.*, 11:467-75 (1985)) were transfected using the calcium phosphate precipitation method described by Van Pel, et al., supra. In addition, rat myeloma cells, IR983F described by Brazin, et al., in Peeters, ed. Protides of the Biological Fluids 29$^{th}$ Colloquium (Pergamin Press, 615-618 (1982), and "Crandell Reese feline kidney," or "CRFK" cells, obtained from the ATCC or "ATCC CCC-94" were transfected via a standard electroporation protocol, i.e., 1 pulse at 40 μsec at 1000 volts.

Twenty-four hours post transfection, the cells were selected via standard limiting dilution culture, in minimal essential medium, using 500 μg/ml hygromycin β.

Example 3

Immunofluorescent Staining of Cells Transformed with the Construct

Following the cell selection described supra, hygromycin resistant cells were tested to determine if they expressed CD134L and the fused antigen on their surfaces.

Indirect immunofluorescent stainings were performed on three types of samples: cells in suspension, cell monolayers grown on glass coverslips and micro-dissected tick salivary glands. All types of samples were fixed in phosphate-buffered saline (PBS) (PBS: 3 mM KCl, 1.5 mM $KH_2PO_4$, 0.14 M NaCl, 6.5 mM $Na_2HPO_4$, pH 7.2) containing 4% (w/v) paraformaldehyde (Merck) for 15 min on ice and then 30 min at room temperature. Where indicated, after washing with PBS, the samples were permeabilized in PBS containing 0.1% (w/v) NP40 (Fluka) for 20 min at 37° C. Immunofluorescent stainings (incubation and washes) were performed in PBS containing 10% (v/v) FCS (PBSF). The samples were incubated at 37° C. for 45 min with primary antibodies. The following primary antibodies were used: a rat monoclonal antibody (Mab) raised against human CD134L (LO-CD134L, Experimental Immunology unit UCL), a mouse Mab raised against human c-Myc (9E10, Becton Dickinson), a mouse Mab raised against human UGRP-1 (MhUGRP-1, Experimental Immunology unit UCL), a mouse Mab raised against human CD94 (HP-3D9, Becton Dickinson) and sera from immunized animals (rat and mice). After three washes, samples were incubated at 37° C. for 30 min with the appropriate secondary conjugate. The following secondary conjugates were used: a FITC-conjugated mouse Mab anti-rat k light chain (MARK-1, Experimental Immunology unit UCL) and an Alexa Fluor® 488 goat anti-mouse IgG (Invitrogen). After three washes with PBSF and a final wash with PBS, samples were either mounted (cell monolayers grown on glass coverslips and micro-dissected tick salivary glands) before microscopic examination (Vanderplasschen et al., Proc Natl Acad Sci USA 95, 7544-9 (1998)) or were analysed by flow cytometry.

The results showed that the fusions to the antigenic proteins did not prevent cell surface expression of CD134L, when fused to its carboxy terminus, and that the fused antigens were also expressed on the cells surfaces (FIG. 2).

Example 4

Animal Immunisation

The data from the prior examples establish that fusion of antigens at the carboxy terminus of a type II protein such as CD134L is an efficient method to induce cell surface expression. Type II carriers, like CD134L, permit the cloning of an antigen in frame with the carboxy terminus, which avoids interference with the anchor signal at the N terminus.

These results suggested testing the potential of these fusion vectors in generating antibodies.

Female Balb-c mice (H-$2^d$), aged between 6 and 8 weeks and a three month old LOU-C rat were used for immunizations with p1.HTR and IR983F cell lines, respectively. All the animals were from specific-pathogen-free colonies bred at the Université catholique de Louvain (Brussels, Belgium) and were submitted to protocols approved by the Institutional Animal Care and Use Committee of the University (Louvain and Liege, Belgium). Balb-c mice were injected subcutaneously with $3.10^5$ P1.HTR cells stably transfected with pCD1-CD134L-IRCAL without any adjuvant. They were then boosted 2 times with $2.10^6$ cells intraperitoneally at two weeks interval. Mice were sacrificed 2 weeks after the last boost. A LOU-C rat was injected intraperitoneally with $10^7$ IR983F cells stably transfected with pCD1-CD134L-A56. Cells were irradiated (5 Gy) before injection in order to avoid their invasiveness in vivo. The immunization was repeated 2 times at two weeks intervals. For the first immunization, cells were suspended in complete Freund's adjuvant. For the 2 last immunizations, cells were suspended in incomplete Freud's adjuvant. Rats were sacrificed 3 days after the last immunization. Serum was collected for serological analysis and the spleen was harvested for Mab production.

Figure 4:
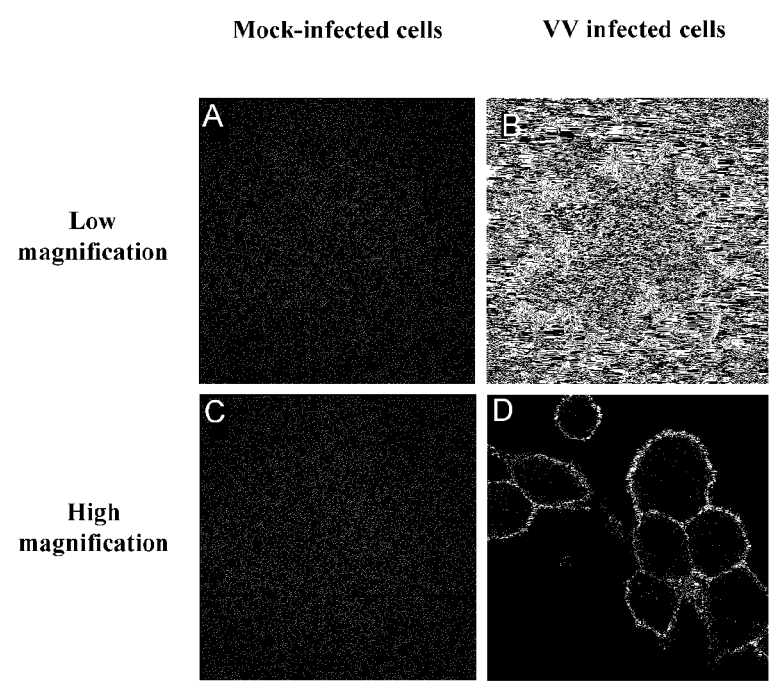
FIG. 4 shows the production of rat Mabs raised against VV A56. Rat Mab A56VV1 raised against VV A56 was one out of the 7 Mabs obtained from a single fusion after immunization with live cells expressing the antigen fused to CD134L. The reactivity of the Mab was tested by indirect immunofluorescent staining of RK13 cells mock-infected or infected cells (Lister strain of VV). The side of panels A-B and C-D corresponds to 1000 and 175 µm of the specimen, respectively.

Rat Mabs were produced as described elsewhere (Bazin, supra). Screening of hybridomas was performed in three steps. Firstly, IR983F cells stably expressing CD134L-A56 were treated for indirect immunofluorescent staining as described above using supernatant of hybridomas as primary antibodies and MARK1-FITC as secondary antibody. Positive staining was detected by flow cytometry. The flow cytometry patterns of the positives clones were similar to these depicted on FIG. 2. Secondly, to determine whether the positive clones secreted antibodies raised against the CD134L carrier or the A56 domain, IR938F cells stably expressing the CD134L (without fused antigen) were stained and analysed (selection of negative clones). Finally, anti-VV A56 hybridomas were confirmed by indirect immunofluorescent staining of RK13 cells infected with the Lister strain of VV (Vanderplasschen et al., Proc Natl Acad Sci USA 95, 7544-9 (1998)); mock-infected cells were used as control (FIG. 4).

The collected mice sera were analyzed for the presence of antibodies specific for the respective antigen via indirect immunofluorescence, as described supra. All of the mice that had been immunized (a total of 10), had detectable antibodies against IRCAL, at titers ranging from 1/512 to 1/4096.

The mouse sera were tested for the presence of antibodies by contact with tick salivary glands. Confocal examination showed that the antibodies recognized a protein that was expressed abundantly in the endoplasmic reticulum and secretory vesicles of the salivary glands.

Serum from the rats contained a high titer (1/8192) of anti-Vaccinia antibodies. As noted, supra, the spleen from the rat was used to produce hybridomas, and then monoclonal antibodies, in accordance with Bazin, supra, incorporated by reference. The hybridomas were screened via indirect immunofluorescence staining of RK13 cells that had been infected with the Lister strain of Vaccinia virus, in accordance with Vanderplasschen, et al., *Proc. Natl. Acad. Sci. USA*, 97:5756-61 (1998).

A single fusion produced seven mAbs which stained the Vaccinia virus plaques strongly.

Example 5

Induction of Auto-Antibodies Raised Against Self Antigens IL-22BP and IL-9

Further experiments were carried out to use the methods of the prior experiments to generate antibodies against IL-22BP, and IL-9.

Coding sequences corresponding to mature murine IL-9 and IL-22BP were amplified from their original cDNA, as described by Van Snick, et al., *J. Exp. Med.*, 169:363-368 (1989), and Weiss, et al., *Genes Immun.*, 5:330-336 (2004), incorporated by reference, via PCR, with primers designed to introduce the XbaI restriction sites. These forward primers are set forth in SEQ ID NOs: 18 and 19, while the reverse primers, which introduced a NotI restriction site and mutated the stop codon, are set forth at SEQ ID NOs: 20 and 21.

The PCR products were digested with XbaI and NotI, and then ligated into the pCD1 plasmid which already contained the other elements referred to supra. The result was a single, open reading frame, encoding a fusion protein between CD134L and IL-9 or IL-22BP.

Example 6

Immunofluorescent Staining of Cells Transformed with the Gene Encoding the Fusion Protein Comprising IL-22BP or IL-9

The resulting vectors were then transfected into P1.HTR cells, using the methods described supra. Twenty-four hours after transfection, selection of cell clones was performed by limiting dilution culture with 500 µg/ml hygromycin B. Cell clones were screened by flow cytometry with a rat monoclonal antibody specific for human CD134L (clone FCL212-1E4), followed by a fluorescein isothiocyanate (FITC)-conjugated mouse anti-rat kappa light chain antibody (clone MARK-1). Alternatively, positive clones were identified by using as primary antibody serum from mice previously immunized with human CD134L, and as secondary antibody, goat anti-mouse FITC-conjugated immunoglobulins. Fluorescence intensity was measured for cells incubated with or without the primary antibody, and cell clones exhibiting the higher fluorescence shift between these two conditions were chosen for injection to mice.

The cells were screened via flow cytometry, also as described, supra. Those cells showing the highest fluorescence shift when comparing results obtained with and without the primary antibody, were used in the following experiments.

Example 7

Animal Immunization Using Cells Transformed with the Gene Encoding the Fusion Protein Comprising IL-22BP or IL-9

Experimental animals were then injected with the cells described supra, to ascertain whether or not antibodies were generated specific to IL-22BP or IL-9.

Syngeneic DBA/2 mice received six, bi-weekly injections of increasing numbers of cells. No adjuvants was used. The first 2 injections were made to the footpads, subcutaneously, and the last four, intraperitoneally. The first injected consisted of $1\times10^5$ cells, and was followed by injections of the same number, then two injection of $1\times10^6$ cells, and then two injections of $5\times10^6$ cells. Mice were bled every two weeks in order to monitor serum antibody titers.

After the first five injections, serum samples were taken from the immunized mice, and the samples were diluted, 1/450. The samples were then incubated, with one of two cell lines (BW5147 or BW.IL-22BP). BW 5147 cells express a cell surface variant of murine IL-22BP. These cells were produced by transfecting BW5147 parent cells with an expression vector that encodes IL-22BP ORF, in fusion with the transmembrane domain of the PDGF receptor. A stably transfected clone known as BW.IL-22BP was also used. See de Mauro, et al., *FEBS Lett.*, 583:1071-1077 (2009), incorporated by reference.

The sera were incubated with the cells and antibodies were detected using a commercially available, goat anti-mouse fluorescent antibody. Anti IL-22BP antibodies could be found in the sera of the immunized mice but not in controls.

Example 8

Inhibition of IL-9 Activity In Vivo

Following the experiments described supra, additional work was carried out to determine if any of the antibodies were inhibitory of IL-22BP function. To determine this, BW.IL22-BP cells were pre-incubated with serial dilutions of the immune sera described supra, for 30 minutes, at room temperature. Then, 3.5 ng/ml of biotinylated murine IL-22 was added, and the mixture was incubated for 45 minutes, at 4° C. Cells were then washed and incubated with phycoerythrin conjugated streptavidin for 30 minutes, at 4° C. The samples were then subjected to standard, FACS analysis.

Sera from control mice did not impact the binding of IL-22, while serum from 2 of 3 mice that had been immunized did significantly antagonize the IL-22 binding, with half-maximal exhibition occurring at serum dilutions of 1/400-1/1,000.

These experiments thus establish that the immunization methodology described herein can produce inhibitory antibodies.

Example 9

Inhibitory Effect of Autoantibodies Directed to IL-9 In Vitro

Further conformance of the efficacy of the method described herein came from experiments in which IL-9 was fused to hCD134L, as described supra. Immunization was carried out as was described for IL-22BP constructs, supra, and inhibitory antibodies were detected using the TS1 bioassay described by Uyttenhove, et al., *Eur. J. Immunol.*, 36:2868-2874 (2006), incorporated by reference.

Sera from all immunized mice inhibited IL-9 induced proliferation of TS-1 cells, at dilutions up to at least 1/1350. The inhibition was shown to be specific, because IL-4 induced proliferation, was not affected at all.

Example 10

Inhibitory Effect of Autoantibodies Directed to IL-9 In Vivo

These experiments were designed to determine if antibodies produced in accordance with methods disclosed herein had inhibitory effects in vivo.

DBA/2 mice were immunized, intraperitoneally, with either contrive cells P1-HTR-CD134L, or P1-HTR-CD134L-mIL-9. The test animals received three intraperitoneal injections of IL-9 (150 ng the first two days, in succession, 30 ng the third day). The mice were bled before the first injection and then at the third day. The concentration of mast cell specific protease mMCP-1 was measured, using commercially available products. (The amount of mMCP-1 is an indicator of IL-9 activity).

The IL-9 induced a significant increase in mMCP-1 levels in control mice, and none in the mice which received the cells transfected with CD134L-mIL-9, thus confirming inhibitory efficacy in vivo.

Example 11

Histocompatibility Restriction

These experiments were designed to determine if histocompatibility antigens are a factor in the methodology discussed herein.

To test this, both syngeneic DBA/2 and allogeneic DBA/2×C57BL/6 mice were treated as described supra, and the antibodies produced were tested for inhibitory effect.

Only half of the C57/BL6 mice produced relevant antibodies, and with low titers, while high titers were found in all DBA/2 and C57BL/6F1 mice, which possess both haplotypes.

Example 12

Immunization of Subject Animal Using Electrotransfer of CD134L Fusion Constructs As a response to the MHC haplotype restriction observed, an electro transfer method was used, in order to induce expression of the fusion construct.

The plasmid pcDNA3, which is commercially available, was used. Vectors were constructed, as described supra, with the CD134L coding sequence fused to IL-22BP. The vectors were then transformed into *E. coli* in order to produce large quantities of the vectors, which were purified using standard methods.

8 weeks old naïve BALB/c mice were prepped for injection by being shaved on their thighs, the day before, and with an injection of alum adjuvant diluted 3 fold in saline buffer, which was then injected in both tibial cranial muscles (25 µl/muscle), of each mouse.

The mice then received 3 electro injections of either the hCD134L-mIL-22BP expression vector or the control, at 3 week intervals. The electro injections were in accordance with Bloquil, et al., *BMC Biotechnol.*, 6:16 (2006), and Vandermeulen, et al., *J. Control Release*, 124:81-87 (2007), incorporated by reference. In brief, 10 µg of the DNA, in 25 µl of saline buffer, was injected into both tibialis of each mouse, all of which had been anesthetized. A 6 mm spaced electrode was then used to deliver 8 electric pulses of 120V (200 V/cm, 20 ms, 2 Hz), to each leg.

Fourteen days after the last injection, animals were bled to analyze the auto antibodies produced.

Figure 5:
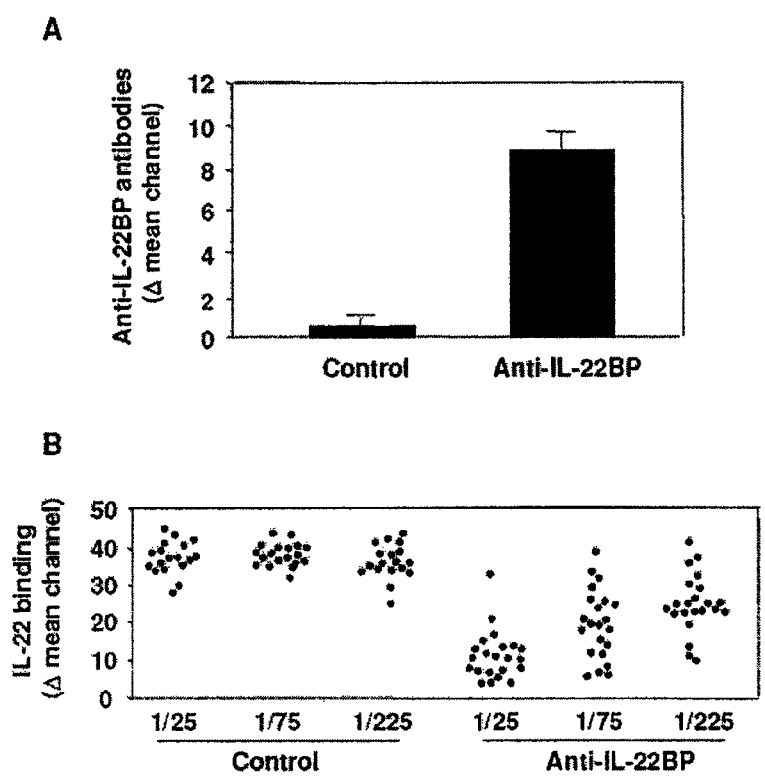
FIG. 5 shows the detection of specific and inhibitory anti-IL-22BP antibodies after DNA electrotransfer. Balb/c mice were immunized three times using electrotransfer with either pcDNA3 (coding for a hCD134L-mIL-22BP fusion protein) or a control vector. Panel A summarizes the results of the analysis of specific antibodies using the flow cytometry assay. Results are presented as mean of delta mean channels for each group (N=18 for control mice, 22 for anti-IL-22BP mice) at a 1/450 dilution. Panel B: the same serum samples were assessed for inhibiting the binding of biotinylated IL-22 on BW.IL22BP cells. IL-22 binding to membrane IL-22BP was determined using the delta mean channel between biotinylated-IL-22 labeled cells preincubated or not with serum dilutions.

Most of the mice produced anti IL-22BP auto antibodies that were detectable at a dilution of 1/450, while inhibiting binding of IL-22 to IL-22BP at higher concentrations. As shown in FIG. 5, most of these mice produced anti-IL-22BP autoantibodies that could be detected at a dilution of 1/450 of the serum (FIG. 5A) and inhibited the binding of IL-22 to IL-22BP at higher concentrations (FIG. 5B). This electrotransfer procedure thereby provides an alternative to whole cell immunization for raising relevant antibodies.

The foregoing describes various features, which include a method for generating antibodies via the use of an expression vector which comprises a nucleic acid molecule which encodes a cell surface type II transmembrane protein, concatenated to a nucleic acid molecule which encodes an antigen of interest, such that a fusion protein is expressed, wherein the construct is in operable linkage with a promoter.

The expression vector may be administered "as is" to a subject animal, or after transformation or transfection into a cell capable of a expressing the fusion protein on its surface.

Exemplary of the cell surface type II membrane proteins disclosed herein is CD134L; however, additional proteins such as, but not being limited to CD10, CD27, CD72, CD153, CD154, and TRAIL may be employed, as well as others that are known to the skilled artisan.

The antigenic coding sequence may be all, or a part of a protein of interest, and may be foreign, or autologous, to the subject animal.

When the expression vector is transformed or transfected into a recipient cell, that cell is preferably treated so as not to be capable of proliferation within the subject.

Other aspects will be clear to the skilled artisan, and need not be reiterated here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

What is claimed is:

1. An expression vector for generating an antibody directed to an antigen, the expression vector comprising a polynucleotide in operable linkage with a promoter, wherein the polynucleotide encodes a fusion protein comprising:
 (i) the polypeptide of SEQ ID NO:2, or a polypeptide having at least 95% amino acid identity to said polypeptide of SEQ ID NO:2 which anchors in a cell membrane as the N-terminal moiety of the fusion protein;
 (ii) an antigenic protein or an antigenic fragment thereof as the C-terminal moiety of the fusion protein; and
 (iii) a linker peptide interposed between (i) and (ii).

2. The expression vector of claim 1, wherein said N-terminal moiety comprises or consists of the amino acid sequence of SEQ ID NO: 2.

3. The expression vector of claim 1, wherein the linker peptide is $(G_4S)_3$.

4. A recombinant cell, transformed or transfected with the expression vector of claim 1.

5. The recombinant cell of claim 4, wherein said cell is a eukaryotic cell.

6. An expression vector for generating an antibody directed to an antigen, the expression vector comprising a polynucleotide encoding a fusion protein comprising an antigenic protein or an antigenic fragment thereof in operable linkage with a promoter, wherein said polynucleotide encoding said fusion protein comprises a nucleic acid sequence encoding said antigenic protein or said antigenic fragment thereof as a C-terminal moiety of said fusion protein and a nucleic acid sequence encoding a polypeptide which anchors in the cell membrane as an N-terminal moiety of said fusion protein, wherein said nucleic acid sequence encoding a polypeptide which anchors in the cell membrane comprises a nucleic acid sequence selected from the group consisting of:
 the polynucleotide of SEQ ID NO:1;
 a polynucleotide having at least 95% nucleic acid identity to said polynucleotide of SEQ ID NO:1, wherein said polynucleotide encodes a polypeptide which anchors in the cell membrane;
 a polynucleotide comprising a nucleotide sequence of SEQ ID NO: 1, wherein said polynucleotide encodes a polypeptide which anchors in the cell membrane,
 wherein the expression vector further comprises a nucleic acid sequence encoding a linker peptide interposed between the nucleic acid sequence encoding said antigenic protein or antigenic fragment thereof and the nucleic acid sequence encoding said polypeptide which anchors in the cell membrane.

7. The expression vector of claim 1, wherein said promoter is selected from the group consisting of SV40 early and late promoters, CMV promoter and promoters of retroviral LTRs, promoter of Rous sarcoma virus ("RSV"), metallothionein promoters, and mouse metallothionein-I promoter.

8. The expression vector of claim 6, wherein the linker peptide is $(G_4S)_3$.

9. An expression vector for generating an antibody directed to an antigen, the expression vector comprising a polynucleotide in operable linkage with a promoter, wherein the polynucleotide encodes a fusion protein comprising:
 (i) a full length mammalian CD134L or a polypeptide having at least 95% amino acid identity to said full length mammalian CD134L which anchors in a cell membrane as the N-terminal moiety of the fusion protein;
 (ii) an antigenic protein or an antigenic fragment thereof as the C-terminal moiety of the fusion protein; and
 (iii) a linker peptide interposed between (i) and (ii).

10. The expression vector of claim 9, wherein the linker peptide is $(G_4S)_3$.

11. An expression vector for generating an antibody directed to an antigen in a subject animal, the expression vector comprising a polynucleotide in operable linkage with a promoter, wherein the polynucleotide encodes a fusion protein comprising:
 (i) CD134L, or a polypeptide having at least 95% amino acid identity to CD134L which anchors in a cell membrane as the N-terminal moiety of the fusion protein;
 (ii) an antigenic protein or antigenic fragment thereof as the C-terminal moiety of the fusion protein; and
 (iii) a linker peptide interposed between (i) and (ii);
 wherein the said CD134L or said polypeptide having at least 95% amino acid identity to CD134L is from a species different from the species of the subject animal.

12. The expression vector of claim 11, wherein the linker peptide is $(G_4S)_3$.

* * * * *